(12) United States Patent
Arnal

(10) Patent No.: US 9,745,246 B2
(45) Date of Patent: Aug. 29, 2017

(54) METHOD FOR PREPARING A SALT OF ACETYLSALICYLIC ACID AND A BASIC AMINO ACID

(71) Applicant: UNITHER PHARMACEUTICALS, Amiens (FR)

(72) Inventor: Thierry Arnal, Dijon (FR)

(73) Assignee: UNITHER PHARMACEUTICALS, Amiens (FR)

( * ) Notice: Subject to any disclaimer, the term of this patent is extended or adjusted under 35 U.S.C. 154(b) by 0 days.

(21) Appl. No.: 15/312,262

(22) PCT Filed: May 28, 2015

(86) PCT No.: PCT/EP2015/061864
§ 371 (c)(1),
(2) Date: Nov. 18, 2016

(87) PCT Pub. No.: WO2015/181304
PCT Pub. Date: Dec. 3, 2015

(65) Prior Publication Data
US 2017/0081270 A1   Mar. 23, 2017

(30) Foreign Application Priority Data
May 28, 2014   (FR) ..................................... 14 54830

(51) Int. Cl.
| C07C 67/52 | (2006.01) |
| C07C 67/28 | (2006.01) |
| C07C 227/16 | (2006.01) |
| C07C 227/42 | (2006.01) |
| C07C 69/157 | (2006.01) |

(52) U.S. Cl.
CPC .............. *C07C 67/28* (2013.01); *C07C 67/52* (2013.01); *C07C 69/157* (2013.01); *C07C 227/16* (2013.01); *C07C 227/42* (2013.01)

(58) Field of Classification Search
CPC ........ C07C 67/52; C07C 67/28; C07C 227/42
See application file for complete search history.

(56) References Cited

U.S. PATENT DOCUMENTS

| 6,773,724 B2 * | 8/2004 | Franckowiak | ........ C07C 229/26 424/400 |
| 2002/0091108 A1 | 7/2002 | Franckowiak et al. | |

FOREIGN PATENT DOCUMENTS

| CN | 102 503 845 A | 6/2012 |
| FR | 2 950 625 A1 | 4/2011 |
| FR | 2 973 370 A1 | 10/2012 |
| FR | 2 992 641 A1 | 1/2014 |
| WO | 2011/039432 A1 | 4/2011 |

\* cited by examiner

*Primary Examiner* — Paul A Zucker
(74) *Attorney, Agent, or Firm* — Im IP Law; C. Andrew Im

(57) ABSTRACT

A method for preparing a salt of acetylsalicylic acid and a basic amino acid. A solution of acetylsalicylic acid and a solution of said basic amino acid are mixed in a reactor, at a temperature lower than or equal to 30° C. at atmospheric pressure. The mixture is created by simultaneously and progressively introducing the acetylsalicylic acid and the basic amino acid into the reactor in amounts that are always equimolar.

17 Claims, 3 Drawing Sheets

METHOD FOR PREPARING A SALT OF ACETYLSALICYLIC ACID AND A BASIC AMINO ACID

RELATED APPLICATIONS

This application is a §371 application from PCT/EP2015/061864 filed May 28, 2015, which claims priority from French Patent Application No. 14 54830 filed May 28, 2014, each of which is incorporated herein by reference in its entirety.

BACKGROUND OF THE INVENTION

The present invention relates to a method for preparing a salt of acetylsalicylic acid and of a basic amino acid, in particular lysine. This method makes it possible in particular to obtain, with a high degree of purity, such a salt having a particularly high stability over time.

Acetylsalicylic acid has been used for many years in the therapeutic field, in particular for its analgesic, anti-inflammatory, antipyretic, anti-rheumatic and platelet aggregation-inhibiting effects. Its solubility in water is however limited, so that it can only be administered in galenical forms containing it in the solid state, and orally.

In order to improve the solubility of acetylsalicylic acid, in particular in water, it has been proposed by the prior art to provide it in the form of a basic amino acid salt. DL-lysine acetylsalicylate thus at the current time constitutes the active ingredient of several medicaments.

A major drawback of DL-lysine acetylsalicylate is its poor stability, in particular because of its hygroscopic nature, so that pharmaceutical formulations which contain it have a limited shelf life. This instability has been explained by a chain of reactions resulting, in the presence of moisture, in the formation of a specific degradation product, salicylic acid, the presence of which in the pharmaceutical formulation is undesirable.

Processes for producing lysine acetylsalicylate aimed at improving the stability of the latter have been proposed by the prior art.

Mention may in particular be made of document US 2002/0091108, which describes a process for producing lysine acetylsalicylate comprising rapid mixing of acetylsalicylic acid and lysine, under conditions of molar excess of lysine, this mixing being followed by cooling of the reaction medium to 0° C. concomitantly with the addition of a large volume of acetone, so as to allow the formation of crystals by stirring of the reaction medium for several hours. However, such a process is lengthy to carry out and it is consequently associated with high production costs. In addition, the degree of purity of the lysine acetylsalicylate that it makes it possible to obtain is insufficient to meet the specifications of the pharmacopeia for use as a medicament active ingredient.

The prior art has alternatively proposed, in particular illustrated by document WO 2011/039432, document FR 2 973 370 or document WO 2011/039432, to prepare DL-lysine acetylsalicylate by mixing acetylsalicylic acid and DL-lysine, under conditions of molar deficiency of DL-lysine. The reaction medium is then diluted in a large volume of acetone, so as to bring about the precipitation of the desired salt. However, it has been noted by the present inventors that the stability of salt of acetylsalicylic acid and lysine thus obtained is insufficient. This process also does not make it possible to obtain this salt with a satisfactory degree of purity.

OBJECT AND SUMMARY OF THE INVENTION

The present invention aims to overcome the drawbacks of the processes described by the prior art for the preparation of DL-lysine acetylsalicylate, in particular those set out above, by providing a method which makes it possible to obtain such a salt, and more generally a salt of acetylsalicylic acid and of a basic amino acid, which exhibits good stability, and a high degree of purity. An additional objective of the invention is for this method to be simple, rapid and inexpensive to carry out.

At the outset of the invention, it has been discovered by the present inventors that, contrary to what is proposed by the prior art, which recommends introducing into the reaction medium amounts of reagents such that one of the two reagents, the acetylsalicylic acid or the basic amino acid, is in excess with respect to the other, so as to influence the pH of the reaction medium, the introduction into the synthesis reactor of strictly equimolar amounts of these two reagents makes it possible, surprisingly, to obtain a salt of the acetylsalicylic acid and of the basic amino acid which has a high degree of purity and is very stable, this being with a high reaction yield.

In particular, it has been discovered by the present inventors that keeping a stoichiometric acetylsalicylic acid/basic amino acid ratio constant at a value of 1:1 in the synthesis reactor makes it possible to substantially entirely prevent the formation of reaction by-products, in particular of salicylic acid, which is the major impurity likely to be generated in the reaction medium. Such a stoichiometric ratio indeed prevents the occurrence of any acid or basic hydrolysis reaction of the salt of acetylsalicylic acid and of the basic amino acid which forms in the synthesis reactor.

Thus, according to the invention, a method for preparing a salt of acetylsalicylic acid and of a basic amino acid is provided, which comprises mixing a solution of acetylsalicylic acid and a solution of the basic amino acid in a reactor, at a temperature of less than or equal to 30° C. at atmospheric pressure. This mixing is carried out by gradual introduction simultaneously of the acetylsalicylic acid solution and of the basic amino acid solution into the reactor, under conditions such that, throughout all the course of this introduction, at each instant the amounts of acetylsalicylic acid and of said basic amino acid introduced into the reactor are equimolar.

BRIEF DESCRIPTION OF THE DRAWINGS

The characteristics and advantages of the method according to the invention will become more clearly apparent on reading the exemplary embodiment hereinafter, provided as a simple illustration, that is in no way limiting, of the invention, with the support of FIGS. 1A to 7, in which.

DETAILED DESCRIPTION OF THE EMBODIMENTS

Figure 1A:
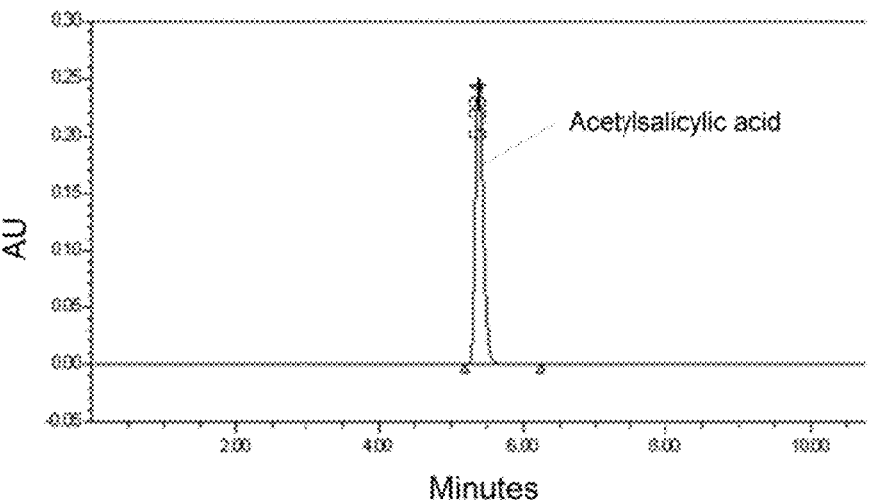
FIG. 1A shows an HPLC chromatogram obtained for a control solution of acetylsalicylic acid at a concentration of 0.1 mg/ml.

The term "equimolar" includes the stoichiometric acetylsalicylic acid/basic amino acid ratios of between 0.99:1 and 1:0.99.

In the present description, the term "amino acid" is intended to mean both natural α-amino acids, i.e. of L configuration, and their enantiomers of D configuration, or a mixture of the L and D forms, as well as homologs, isomers and derivatives thereof, such as amino acids comprising a protecting group.

In the present description, a basic amino acid is defined conventionally in itself as an amino acid with a side chain that is positively charged at neutral pH.

The basic amino acid can in particular be chosen from ionizable polar amino acids, more particularly dibasic amino acids.

Preferentially, the basic amino acid is lysine, in particular L-lysine or DL-lysine, where appropriate in monohydrate form, or homologs, isomers or derivatives thereof.

The amino acid can alternatively be chosen from arginine, histidine and ornithine, or homologs, isomers or derivatives thereof.

The acetylsalicylic acid can be introduced into the synthesis reactor in solution in a water-miscible solvent, such as an alcohol, in particular methanol, ethanol or isopropanol, an ether, such as tetrahydrofuran, or a ketone, in particular acetone, or in a mixture of such solvents. Preferentially, a solution of acetylsalicylic acid in acetone is used.

The basic amino acid is, for its part, preferably introduced into the reactor in an aqueous solution, obtained in particular by dissolving the basic amino acid in distilled water.

The parameters which make it possible to control the number of moles of each of the reagents introduced into the reactor are the molar concentration of the initial solution of reagent, as well as its flow rate of introduction into the reactor. According to the present invention, the values of each of these parameters are chosen according to one another, so as to ensure that, at each instant, the same molar amount of acetylsalicylic acid and of basic amino acid is introduced into the reactor. It is within the scope of those skilled in the art to make such a combined choice of values for these parameters.

In particular embodiments of the invention, the acetylsalicylic acid solution comprises from 0.8 to 0.9 mol/l of acetylsalicylic acid. Such concentrations allow in particular optimal dissolution of the acetylsalicylic acid in the acetone, in particular under temperature conditions of between 10 and 30° C.

The basic amino acid solution can, for its part, comprise a concentration of between 4.5 mol/l and 5.5 mol/l of said basic amino acid. Such a concentration range in particular advantageously makes it possible, on the one hand, to form a solution the viscosity of which is sufficiently low for making it possible to easily introduce it into the reactor, by means of a metering pump conventional in itself, and, on the other hand, when the solution is an aqueous solution, to limit the water content thereof to a value which is not capable of preventing the subsequent crystallization, from the reaction medium, of the salt of acetylsalicylic acid and of the basic amino acid forming during the reaction.

In particular embodiments of the method according to the invention, the gradual introduction of the acetylsalicylic acid solution and of the basic amino acid solution into the reactor is carried out with a flow rate of introduction of the acetylsalicylic acid solution of between 10 and 50 l/h, and a flow rate of introduction of the basic amino acid solution of between 2 and 15 l/h.

These introduction flow rates may be constant or variable. In the latter case, their variation profiles are similar.

When the introduction of the solutions of reagents into the reactor is carried out by means of metering pumps, the frequencies of these pumps are in particular adjusted so as to be substantially identical to one another, so as to enable, at each instant, the introduction into the reactor of strictly equimolar amounts of reagents.

During the phase of introduction of the solutions of reagents into the synthesis reactor, the exothermicity of the reaction occurring in said reactor, from the acetylsalicylic acid and the basic amino acid, is controlled by controlling the temperature of the reaction medium, ensuring that the temperature thereof preferentially does not exceed a value of 20° C. at atmospheric pressure. Preferably, the temperature of the reaction medium contained in the reactor is maintained between −10° C. and 20° C., at atmospheric pressure, throughout all the phase of introduction of the solutions of reagents into the reactor. This controlling of the temperature of the reaction medium can be carried out by any means conventional in itself, in particular by using a reactor comprising a cooling jacket, inside which circulates a liquid refrigerant of appropriate temperature.

The temperature range recommended by the present invention not only makes it possible to prevent the formation of unwanted by-products that would be liable to be brought about by too high a temperature of the reaction medium, but, in addition, it in particular and entirely advantageously promotes good crystallization of the salt of acetylsalicylic and basic amino acid forming in the reactor. This salt will, for convenience, be denoted in the remainder of the present description by the expression "salt of interest".

Preferentially, light stirring, for example between approximately 200 and 500 rpm when the reactor used has a capacity of three liters, is maintained in the reactor throughout the phase of introduction of the solutions of reagents.

In particularly preferred embodiments of the invention, the method comprises a "crystal maturation" phase, according to which the reaction medium, formed at the end of the phase of introduction of the acetylsalicylic acid solution and of the basic amino acid solution into the reactor, is kept with stirring at a temperature of between −15° C. and 20° C., preferably approximately −10° C., for a period of between 30 and 90 minutes, preferably for 1 hour. The reaction medium preferentially undergoes no modification prior to this phase of maintaining the stirring. In particular, no solvent is added thereto beforehand, nor is any other component aimed in particular at promoting the precipitation of the salt of acetylsalicylic acid and of the basic amino acid in the form of crystals from the reaction medium. Thus, according to the invention, the crystal maturation phase is carried out directly on the reaction medium resulting from the mixing of the acetylsalicylic acid solution and the basic amino acid solution, without any intermediate step. This phase can also advantageously be carried out in the synthesis reactor itself.

In that respect, the method according to the invention proves to be much more advantageous than the processes recommended by the prior art, which comprise a phase of precipitating the salt of acetylsalicylic acid and the basic amino acid by transferring the reaction medium into a second reactor, and mixing with a large volume of acetone.

On the contrary, according to the invention, the precipitation of the salt of acetylsalicylic acid and the basic amino acid is carried out in situ, without prior dilution of the reaction medium, including when the latter comprises as solvent a mixture of an organic solvent, in particular acetone, and of water. Surprisingly, it has been discovered by the present inventors that, under such conditions, the precipitation of the salt of interest, although this salt is very soluble in water, takes place without any drop in yield, and without any impact on the quality of the salt formed.

The controlling, in accordance with the invention, of the temperature of the reaction medium during the crystal maturation phase makes it possible in particular to prevent such dissolution of the salt of interest in the mixture of solvents contained in the reactor, and thus to increase the yield of the method according to the invention.

In particular embodiments of the invention, at the end of the crystal maturation phase, the solid contained in the reaction medium is isolated. For this purpose, any conventional technique can be carried out, for example the centrifugation technique or the filtration technique.

Where appropriate, the solid thus isolated can be washed, one or more times, by means of an organic solvent, such as an alcohol, a ketone, or a mixture of such solvents, so as to remove from it any impurities, such as for example the main degradation product of the salt of interest, salicylic acid.

After the optional washing step(s), the solid phase is again separated from the liquid phase, and can be subjected to drying.

In variants of the invention, at the end of the crystal maturation phase, the solid contained in the reaction medium is subjected to a step of recrystallization of the salt of acetylsalicylic acid and said basic amino acid, where appropriate after having been isolated from the reaction medium, and then where appropriate washed by means of an organic solvent.

Such a recrystallization step advantageously makes it possible to obtain a better particle size heterogeneity of the salt of acetylsalicylic acid and the basic amino acid obtained.

It can be carried out by any method known to those skilled in the art.

Preferentially, it is carried out in a mixture of solvents comprising water and at least one alcohol, for example ethanol or 2-propanol.

By way of example, the recrystallization step can be carried out by means of the succession of the following phases, the solid having been isolated beforehand from the reaction medium, for example by filtration:

suspension of the solid in alcohol, for example in two volumes of alcohol, addition of water, for example of two volumes of water, to the mixture obtained, so as to dissolve the product, addition of a further amount of alcohol, for example of four volumes of alcohol, first cooling phase, for example to a temperature of approximately 25° C., and initiation of the recrystallization, second cooling phase, for example to a temperature of approximately 5° C., for a few minutes.

Such operating conditions advantageously make it possible to obtain crystals of salt of acetylsalicylic acid and the basic amino acid of uniform size, with a relatively low specific surface area, such that the possible absorption, at the surface of the crystals obtained, of residual solvents prejudicial to the stability of the product during its storage, is advantageously minimized.

At the end of the crystallization step, the solid obtained, consisting of the salt of acetylsalicylic acid and the basic amino acid with a high degree of purity, is separated from the liquid phase, and can be subjected to a drying step.

In particularly preferred embodiments of the invention, the method preferably comprises a final step of drying the salt of acetylsalicylic acid and the basic amino acid obtained.

According to the present invention, the drying is preferentially carried out in at least two successive steps, comprising:

a first step of drying with stirring, preferably with light stirring, at a first pressure P1 of between 200 and 300 mbar, preferably of approximately 250 mbar, and at a first temperature T1 of between 20 and 25° C., for a period of between 90 and 250 minutes, preferably of approximately 230 minutes comprising a period of 15 minutes of temperature increase;

a second step of drying with stirring, preferably with light stirring, at a second pressure P2 of between 10 and 30 mbar, preferably of approximately 20 mbar, and at a second temperature T2 of between 40 and 50° C., preferably of approximately 42° C., for a period of between 90 and 250 minutes, preferably of approximately 235 minutes comprising a period of 15 minutes of temperature increase.

Such a two-step process advantageously makes it possible to form a salt of acetylsalicylic acid and the basic amino acid which comprises a very low residual water content, less than 0.5%, so that it has very good stability over time, when stored under inert atmosphere.

Such conditions of gradual drying, in successive steps of temperature increase and of pressure decrease, indeed make it possible to dry the salt of interest rapidly and efficiently, and to obtain it in the form of a crystalline fine powder. They in particular advantageously make it possible, on the one hand, to prevent any degradation of the salt of interest, and on the other hand, to prevent the formation of granules of the salt of interest, which could not be dried to core unless under a large increase in temperature capable of causing the degradation thereof.

In particular embodiments of the invention, an intermediate drying step is carried out between the first drying step and the second drying step, said intermediate drying step being carried out with stirring, preferably with light stirring, at a temperature comprised between the first temperature T1 and the second temperature T2, preferably between 30 and 40° C. and preferentially of approximately 32° C., and:

at a pressure of between 200 and 300 mbar, preferably substantially equal to the first pressure P1, for a period of between 60 and 100 minutes, preferably of approximately 75 minutes comprising a period of 15 minutes of temperature increase, then at a pressure of between 10 and 30 mbar, preferably substantially equal to the second pressure P2, for a period of between 60 and 100 minutes, preferably of approximately 60 minutes.

The method corresponding to such characteristics advantageously makes it possible to obtain a salt of acetylsalicylic acid and a basic amino acid, in particular lysine acetylsalicylate, which meets the specifications of the pharmacopeia, in particular in terms of low residual water and solvent contents, and of low contents of impurities, in particular of salicylic acid.

The method according to the invention is preferably carried out in batches. Preferentially, all of its steps are carried out under an inert atmosphere. In particular embodiments of the invention, they are also carried out under sterile conditions.

The method according to the invention is advantageously easy and quick to carry out, what is more at low cost. Any device conventional in itself can be used for this purpose, in particular the conventional devices for producing pharmaceutical active ingredients on an industrial scale.

In particular, the steps of filtering, washing and drying the salt of acetylsalicylic acid and the basic amino acid can be carried out in one and the same piece of equipment, such as a filter-drier equipped with controlled stirring means.

According to another aspect, the present invention relates to a composition obtained by means of a method according to the invention having one or more of the characteristics above.

This composition comprises in particular an acetylsalicylic acid salt content of between 97% and 100%, in particular of between 98% and 100%. It has a water content of less than 0.3%, and a salicylic acid content of less than 0.3%. Conditioned hermetically under an inert atmosphere, it remains stable for at least 6 months.

This composition can in particular be used for the production of a pharmaceutical formulation comprising it in an effective amount in a pharmaceutically acceptable carrier, where appropriate in combination with other active ingredients, and any additive conventional in itself.

It has applications in particular as an active ingredient with an analgesic, antipyretic, anti-inflammatory, antirheumatic, platelet aggregation-inhibiting, etc. effect, for the curative and/or preventive treatment of various pathological conditions, such as rheumatism, neuralgia, myalgia, migraines, cardiovascular and cerebrovascular diseases, etc.

The invention also relates to a salt of acetylsalicylic acid and of a basic amino acid, in particular lysine, which is in a granular form, more specifically in the form of a powder of crystals, and which is obtainable by carrying out a method according to the invention, having one or more of the characteristics above, comprising a recrystallization step. This powder is characterized by an acetylsalicylic acid salt content of between 97% and 100%, a water content of less than 0.3% and a salicylic acid content of less than 0.3%.

It also has an average grain diameter of between 100 and 110 μm, measured for example using a Malvern device under normal operating conditions, and a high crystal size uniformity. The crystals having such a size advantageously have in particular a relatively low specific surface area, such that the possibility of any absorption at their surface, of residual solvents prejudicial to the stability of the product during the storage thereof, is minimized.

Example 1—Method for Synthesizing DL-Lysine Acetylsalicylate

DL-lysine acetylsalicylate (III) is prepared from acetylsalicylic acid (I) and DL-lysine (II), according to the reaction scheme:

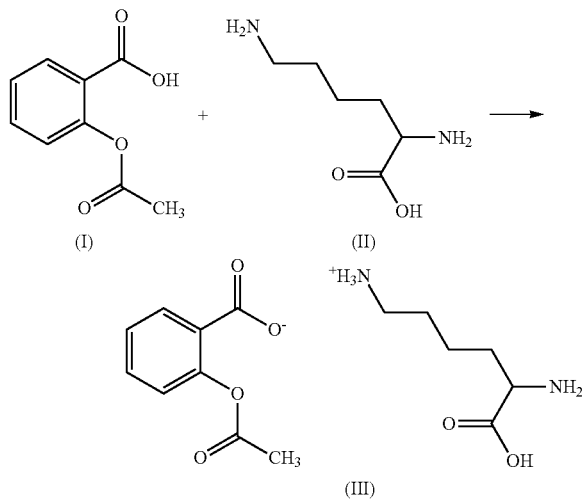

by means of the method in accordance with the invention described hereinafter.

Preparation of the Reagent Solutions

The starting reagents are acetylsalicylic acid and DL-lysine.

A solution of acetylsalicylic acid at 17.7% (w/w) in acetone is prepared, at a temperature of between 10 and 30° C., in a first container in which nitrogen flushing is applied. For this purpose, 400 g of acetylsalicylic acid, in the form of a white powder, and then 1856 g of acetone are introduced into the container. The mixture is stirred, at 450 rpm, until the acetylsalicylic acid has completely dissolved. A clear and colorless solution, hereinafter referred to as solution A, is obtained. This solution has a density at 20° C. of between 0.850 and 0.860 g/cm$^3$.

Moreover, an aqueous solution of DL-lysine at 33% (w/w) in water is prepared in a second container, at a temperature between −10 and 40° C. For this purpose, 600 g of a solution of DL-lysine at 50% in water are mixed with 308.85 g of osmosed water. The mixture is stirred until a clear and transparent solution, hereinafter referred to as solution L, is obtained. This solution has a density at 20° C. of between 1.080 and 1.090 g/cm$^3$.

Mixing of the Reagent Solutions and Maturation of the Crystals

The synthesis reactor used for the formation of the DL-lysine acetylsalicylate is a double-jacketed reactor under nitrogen flushing, equipped with two-stage stirring and connected to a cryothermostat.

IKA metering pumps are used to introduce the reagent solutions into the reactor. These pumps are adjusted, in terms of piston travel percentage and frequency, to provide respective flow rates of 13.07 l/h for solution A and 4.47 l/h for solution L. These respective flow rates enable the simultaneous introduction into the reactor of equimolar amounts of acetylsalicylic acid and of DL-lysine (in a proportion of 0.182 mol·min$^{-1}$ of each of the reagents). The frequencies of the metering pumps are adjusted substantially identical to one another, so as to ensure that the amounts of the reagents introduced into the reactor make it possible to maintain equimolar amounts of the reagents in the reactor throughout the mixing time.

Prior to the introduction of solution A and of solution L into the reactor, the cryothermostat is turned on to ensure the circulation, in the jacket of the reactor, of a fluid refrigerant at a temperature of less than or equal to −15° C.

The metering pumps are then activated simultaneously, so as to introduce solution A and solution L into the reactor, in a ratio of the two reagents that is equimolar at each instant t.

During this step, the reaction medium is stirred, at a relatively low first stirring speed, of between 240 and 450 rpm, so as not to break the crystals which form.

During these steps, the temperature of the reaction medium is maintained between −10° C. and 15° C. More specifically, it is measured at 10.1° C. The salt formation reaction takes place gradually as the reagent solutions are introduced into the reactor.

When the volume of the reaction medium reaches 2.5 l, the operation of the metering pumps is interrupted.

The following have been introduced into the reactor: 1.708 l of solution A and 0.584 l of solution L.

The reaction medium contained in the reactor is cooled to −10° C. with reduced stirring, at a stirring speed of 360 rpm. The reaction medium is kept stirring at this speed at −10° C. for 1 h.

Filtrations and Washing

The reaction medium is transferred into a filter-drier-stirrer.

This filter-drier is equipped with a double jacket connected to a cryothermostat, for controlling the temperature inside said filter-drier.

The reaction medium is subjected to a first filtration step under reduced pressure of 270 mbar, with stirring. This filtration is carried out in several sequences, so as to perform paste formation and then smoothing of the product contained in the filter. After approximately 30 min, a uniform product that can be easily stirred is obtained in the filter.

The product is subjected to washing with 2-propanol, a volume of which corresponding to 1.5 times the weight of DL-lysine acetylsalicylate obtained, i.e. 501.50 g of 2-propanol, is introduced into the filter.

The mixture obtained is stirred for 10 min, at a stirring speed of 360 rpm and under reduced pressure, so as to obtain a uniform suspension.

This mixture is then subjected to a second filtration step under reduced pressure of 270 mbar, with stirring. This filtration is carried out in several sequences, so as to perform paste formation and then smoothing of the product contained in the filter. After approximately 60 min, a uniform product that can be easily stirred is obtained in the filter.

A sample of this product is taken and analyzed in terms of its composition, as described in detail hereafter in the description.

Drying

The drying of the reaction product is carried out in three distinct phases, as described in detail hereinafter.

All of these steps are carried out with stirring, in the filter-drier, in which a reduced pressure is applied by a pipe connected at the level of the lid, above the product to be dried.

Phase 1:

In phase 1, the pressure applied in the filter-drier is approximately 240 mbar, and the temperature is 22° C. The stirring speed is 10 rpm. This sequence has a duration of 135 min, including 15 min of temperature increase up to 22° C., and 120 min of maintaining at this temperature.

Phase 2:

In phase 2, the temperature is increased, over a period of 15 min, until it reaches a value of 32° C. The stirring is maintained at 10 rpm. The pressure is maintained at 240 mbar for 60 min, then at a value of less than or equal to 20 mbar for a further 60 min.

Phase 3:

The temperature is increased, over a period of 15 min, until it reaches a value of 42° C. The stirring is maintained at 10 rpm, and the pressure at a value of less than or equal to 20 mbar for 120 min.

In total, 427.88 g (92.4% yield) of a dry product, which is in the form of a white crystalline fine powder, hereinafter referred to as ASL, are obtained. A sample of this dry product is taken from the filter, under an inert atmosphere, and subjected to analysis, as described in detail hereinafter.

The DL-lysine acetylsalicylate thus obtained is packaged in a hermetically sealed bottle under nitrogen flushing. It complies with the specifications of the pharmacopeia for use in the pharmaceutical field.

Example 2—Analysis of the Product Obtained 2.1. Analysis by HPLC—Acetylsalicylic Acid and Salicylic Acid Contents The analysis by HPLC is carried out according to the method of the European Pharmacopeia 2.2.29, as indicated below.

For this purpose, the following operating conditions are implemented.

For Titration of the Acetylsalicylic Acid
Column: Luna C18 (reference: 00G-4041-E0)
  Length: 250 mm
  Internal diameter: 4.6 mm
  Particle size: 5 μm
Mobile phase: Acetonitrile: 400 V
  Water: 600 V
  85% Orthophosphoric acid: 2 V
Flow rate: 1.0 ml/min
Temperature: 25° C.
Volume injected: 10 μl
Wavelength: 237 nm
Analysis time: 15 minutes
Acetylsalicylic acid retention time: approximately 5.4 min A control solution is prepared by dissolving 50.0 mg of acetylsalicylic acid in 50 ml of mobile phase, then diluting 5 ml of the solution obtained in 50 ml of mobile phase.

The solutions of the samples of ASL to be tested for their acetylsalicylic acid content are prepared by dissolving 90.6 mg of sample in 50 ml of mobile phase, then diluting 5 ml of the solution obtained in 50 ml of mobile phase.

The acetylsalicylic acid content of each sample of ASL is obtained by means of the following equation:

$$T = \frac{Pt}{Pe} \times \frac{T}{100} \times \frac{Ae}{At} \times \frac{100-Ht}{100-He} \times \frac{326.3}{180.16} \times 100$$

wherein:

Ae represents the area of the peak of acetylsalicylic acid in the chromatogram of the solution of sample to be tested, At represents the area of the peak of acetylsalicylic acid in the chromatogram of the control solution, Pt represents the weight of the acetylsalicylic acid in the control solution in mg, T represents the titer of the acetylsalicylic acid in %, Pe represents the weight of the solution of sample in mg, Ht represents the halogen loss of the control in %, and He represents the halogen loss of the starting material in %.

Figure 1B:
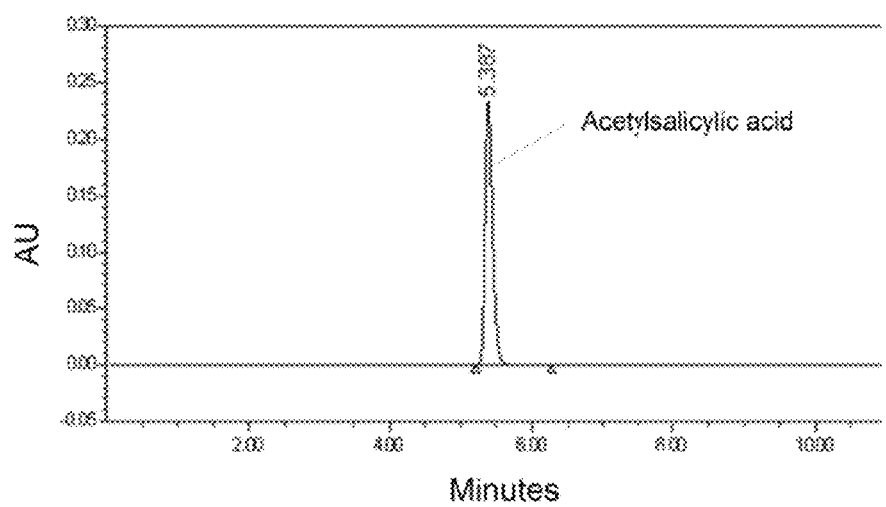
FIG. 1B shows an HPLC chromatogram obtained for a solution of DL-lysine acetylsalicylate obtained by means of a method in accordance with the invention, at a concentration of 0.18 mg/ml.

The chromatograms obtained, for the acetylsalicylic acid and for the dry ASL obtained according to example 1 above, are shown respectively in FIGS. 1A and 1B. An acetylsalicylic acid titer of 98.3% is deduced therefrom. This value complies with the specifications of the European Pharmacopeia (2.2.29), which requires a titer between 97.0% and 101.0%.

For Titration of the Salicylic Acid (Impurity)

The operating conditions are identical to those indicated above for titration of the acetylsalicylic acid, with the exception of:

Mobile phase: 85% orthophosphoric acid: 4 V

Analysis time: 30 min for the tests and 15 min for the controls

Retention time: salicylic acid: approximately 8.3 min
acetylsalicylic acid: approximately 5.8 min A control solution of salicylic acid at 0.3% is prepared by dissolving 150.0 mg of salicylic acid in 50 ml of mobile phase, then diluting 1 ml of the solution obtained in 100 ml of mobile phase.

The solutions of the samples of ASL to be tested for their acetylsalicylic acid content are prepared by dissolving 100 mg of sample in 10 ml of mobile phase.

The salicylic acid content of each sample of ASL is obtained by means of the following equation:

$$T = \frac{Pt \times T}{100} \times \frac{Ae}{At} \times \frac{1}{Pe} \times \frac{1-Ht}{1-He} \times \frac{10}{5000} \times 100$$

wherein

Ae represents the area of the peak of salicylic acid in the chromatogram of the solution of sample to be tested, At represents the area of the peak of salicylic acid in the chromatogram of the control solution, Pt represents the weight of the salicylic acid in the control solution in mg, T represents the titer of the salicylic acid in %, Pe represents the weight of the solution of sample in mg, Ht represents the halogen loss of the control in %, and He represents the halogen loss of the starting material in %.

Figure 2A:
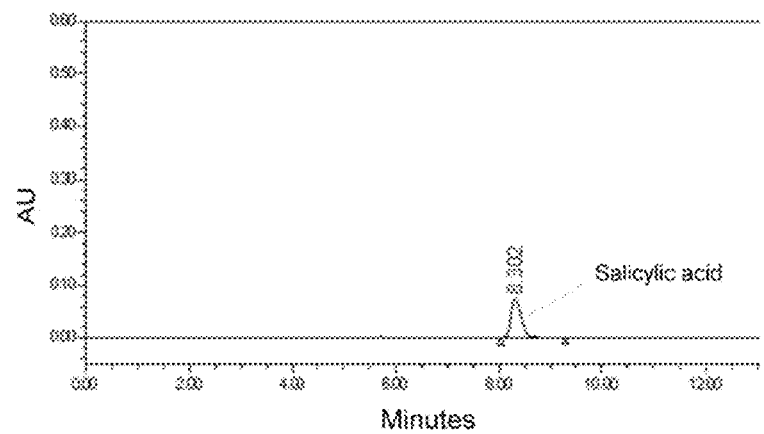
FIG. 2A shows an HPLC chromatogram obtained for a control solution of salicylic acid at a concentration of 0.03 mg/ml.
Figure 2B:
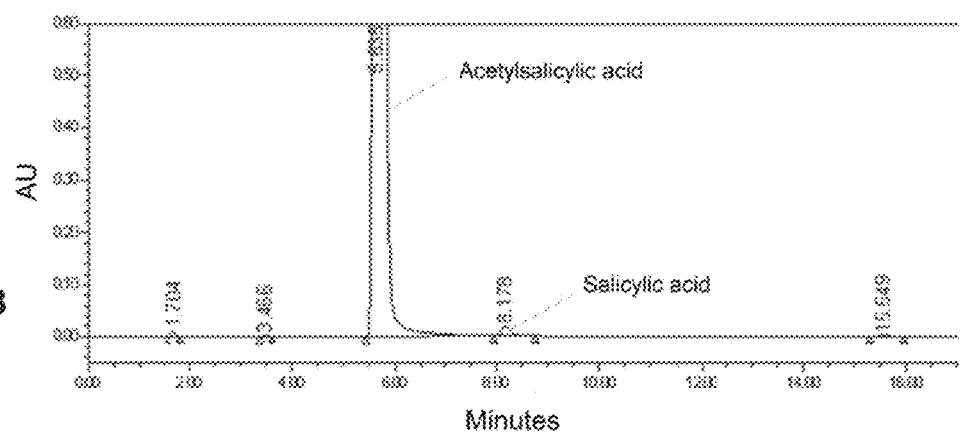
FIG. 2B shows an HPLC chromatogram obtained for a solution of DL-lysine acetylsalicylate obtained by means of a method in accordance with the invention, before drying, at a concentration of 10 mg/ml.
Figure 2C:
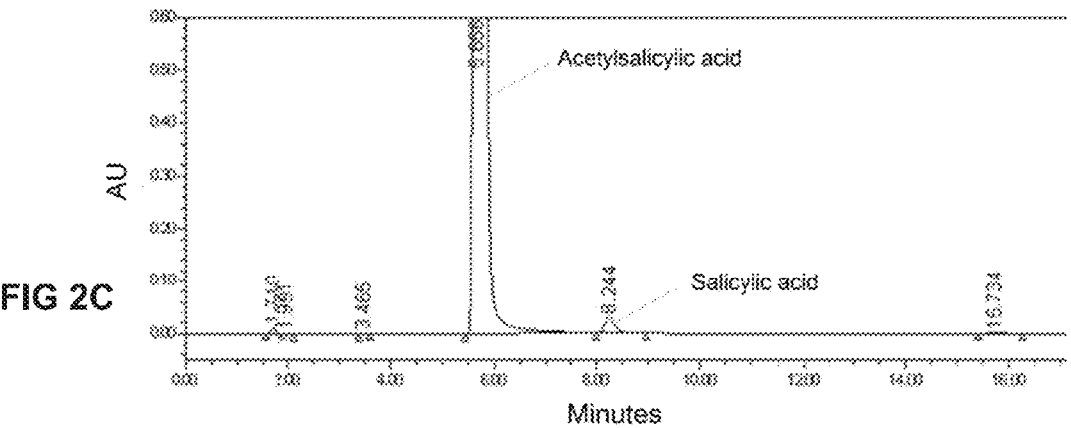
FIG. 2C shows an HPLC chromatogram obtained for a solution of DL-lysine acetylsalicylate obtained by means of a method in accordance with the invention, after drying, at a concentration of 10 mg/ml.

The chromatograms obtained, for the salicylic acid, for the ASL before drying and for the dry ASL which are obtained according to example 1 above, are shown respectively in FIGS. 2A, 2B and 2C. A salicylic acid titer of 0.08% for the ASL before drying, and of 0.13% for the dry ASL, are deduced therefrom. These values comply with the specifications of the European Pharmacopeia (2.2.29), which requires a salicylic acid titer of less than or equal to 0.3%.

2.2. Other Analyses

The other analyses hereinafter are also carried out on the dry ASL obtained in example 1.

Operating Protocols

Residual moisture content: halogen loss on desiccation in a desiccator 5 g/90° C./20 min.

Water content: according to European Pharmacopeia 2.5.12, titration carried out by Karl Fisher titration on 1 g of ASL.

Sulfated ash: according to European Pharmacopeia 2.4.14, on 1.0 g of ASL in a crucible of mass $m_{crucible}$ (initial total mass of the crucible and of the ASL: $m_{test}$), with 1 ml of the sulfuric acid reagent R, heating on hot plates until complete carbonization is obtained, for approximately 4 h, then, in a furnace, temperature increase up to 600° C. over the course of 2 h and maintaining at 600° C. for 30 min. After cooling, weighing is carried out (final total mass of the crucible and of the sample: $m_{final}$). The percentage residue is obtained by means of the following equation:

$$\% \text{ residue} = \frac{m_{final} - m_{crucible}}{m_{test}} \times 100$$

Chloride: according to European Pharmacopeia 2.4.4, with the reagents: dilute nitric acid R, silver nitrate solution R2, stock solution of chlorides.

A solution containing 5 ppm of chloride (R) is prepared by diluting 1 ml of stock solution of chlorides in 100 ml of water R.

The solution to be tested is prepared by dissolving 0.33 g of ASL in 15 ml of water R. 1 ml of dilute nitric acid R is added and this mixture is poured in a single step into a test tube containing 1 ml of silver nitrate solution R2.

The control solution is prepared in the same way, using a mixture of 10 ml of solution containing 5 ppm of chloride R and 5 ml of water R.

A blank is prepared under the same conditions with 15 ml of water R.

After 5 min in the dark, the opalescence of the solution to be tested is examined and compared with that of the control.

Heavy metals: according to European Pharmacopeia 2.4.8, method A, with the reagents: buffer solution pH 3.5 R, thioacetamide solution R at 4%, glycerin reagent, lead stock solution.

The glycerin reagent is obtained by mixing 5 ml of water R, 15 ml of 1M sodium hydroxide and 20 ml of 85% glycerol R.

The thioacetamide reagent R is obtained by mixing 0.2 ml of thioacetamide solution R and 1 ml of glycerin reagent.

The solution containing 2 ppm of lead is prepared by diluting 0.2 ml of lead stock solution in 100 ml of water R.

The solution to be tested is prepared by dissolving 4.0 g of ASL in 20 ml of water R.

The control solution is prepared by mixing 10 ml of solution containing 2 ppm of lead and 2 ml of solution to be tested.

A blank is prepared under the same conditions with 10 ml of water R and 2 ml of solution to be tested.

2 ml of buffer solution pH 3.5 R, then 1.2 ml of thioacetamide reagent R are mixed with each solution.

After 5 min in the dark, the opalescence of the solution to be tested is examined and compared with that of the control and with that of the blank.

according to European Pharmacopeia 2.2.3, a solution is reconstituted by dissolving 1 g of ASL in 10 ml of water free of carbon dioxide, with stirring for 30 s. Its appearance is evaluated and its pH is measured.

Content of each unknown impurity: by HPLC assay, according to the operating protocol described above. The content of each impurity is determined by means of the following equation:

$$T = \frac{PtASL \times T}{100} \times \frac{Ae}{AtASL} \times \frac{1}{Pe} \times \frac{1-Ht}{1-He} \times \frac{10}{5000} \times 100$$

wherein:
Ae represents the area of the peak of the impurity in the chromatogram of the solution of sample to be tested,
AtASL represents the area of the peak of ASL in the chromatogram of the control solution at 0.1%,
PtASL represents the weight of ASL in the control solution in mg,
T represents the titer of the ASL in %,
Pe represents the weight of the solution of sample in mg,
Ht represents the halogen loss of the salicylic acid control in %, and
He represents the halogen loss of the starting material in %.

Residual solvents by HS-GC, according to European Pharmacopeia 2.2.28. The operating conditions are the following:
Headspace conditions:
Oven temperature: 80° C.,
Loop temperature: 80° C.,
Transfer line temperature: 85° C.,
GC cycle: 20 min,
Vial equilibration time: 15 min,
Pressurization time: 0.5 min,
Loop filling time: 0.04 min,
Loop equilibration time: 0.5 min,
Injection time: 0.5 min,
Vial volume: 20 ml, and
Sample volume: 5 ml.
Chromatographic conditions:
Column: DB-FFAP (reference: 122-3232)
    Length: 30 m
    Internal diameter: 250 μm
    Film thickness: 0.25 μm
Vector gas: helium
Flow rate: 1.50 ml/min
Injector temperature: 150° C.
Mode: split
Split ratio: 1/2
Oven temperature: 80° C. for 2.30 min, then gradient of 30° C./min up to a temperature of 250° C., for a total time of 7.79 min
Detector (FID) temperature: 300° C.
$H_2$ flow rate: 45 ml/min
$O_2$ flow rate: 400 ml/min
Constant makeup: 30.0 ml/min
Analysis time: 8.0 min
Retention time: acetone: approximately 1.7 min
    isopropanol: approximately 1.9 min.

A control solution of acetone at 5000 ppm is prepared by dissolving 500.0 mg of acetone in 50 ml of water and then diluting 5 ml of this solution in 100 ml of water.

A control solution of isopropanol at 5000 ppm is prepared by dissolving 500.0 mg of isopropanol in 50 ml of water and then diluting 5 ml of this solution in 100 ml of water.

A control solution of ethanol at 5000 ppm is prepared by dissolving 500.0 mg of ethanol in 50 ml of water and then diluting 5 ml of this solution in 100 ml of water.

The solution to be tested is prepared by dissolving 2 g of ASL in 20 ml of water.

The solvent content in the ASL is determined by means of the equation:

$$T = \frac{Pt \times T}{100} \times \frac{Ae}{At} \times \frac{1}{Pe} \times \frac{20}{1000} \times 10^6$$

wherein:
Ae represents the area of the solvent peak in the chromatogram of the solution of sample to be tested,
At represents the area of the solvent peak in the chromatogram of the control solution at 0.1%,
Pt represents the weight of solvent in the control solution in mg,
T represents the solvent titer in %, and
Pe represents the weight of the solution of sample in mg Results The results obtained, for the dry ASL obtained in example 1, are indicated in table 1 hereinafter. The European Pharmacopeia specifications are also indicated in this table.

TABLE 1 result of analyses of DL-lysine acetylsalicylate obtained by means of a method according to one particular embodiment of the invention

| Test | Specifications | ASL |
|---|---|---|
| Appearance of the powder | Crystalline white and fine | Complies |
| Appearance of the reconstituted solution | Transparent solution | Complies |
| pH of the reconstituted solution | 4.5 to 6.5 | 5.9 |
| Water content | ≤0.5% | 0.4% |
| Residual moisture content | ≤1.0% | 0.4% |
| Impurities | | |
| Other unknown impurity | ≤0.1% | 0.02% |
| Sum of the impurities | — | 0.15% |
| Residual solvents | ≤0.5% | 0.19% |

It emerges from these results, combined with those obtained for the HPLC assay of the acetylsalicylic acid and salicylic acid contents indicated above, that the method in accordance with the present invention makes it possible to obtain, with a high yield, a salt of acetylsalicylic acid and DL-lysine with a high degree of purity, and in accordance with the European Pharmacopeia specifications.

2.3. Particle Size

The particle size was analyzed by means of a Scirocco 2000 instrument (Malvern), according to a protocol conventional in itself.

Figure 3:
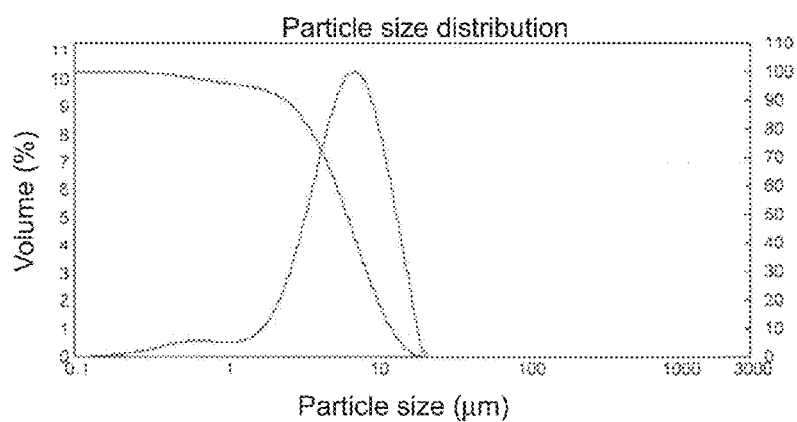
FIG. 3 is a graph indicating the size and the size distribution of the particles of a powder of DL-lysine acetylsalicylate obtained by means of a method in accordance with the invention, after drying.

The results obtained, in terms of particle size, are shown in FIG. 3. The average particle size is 6.931 μm.

Figure 4:
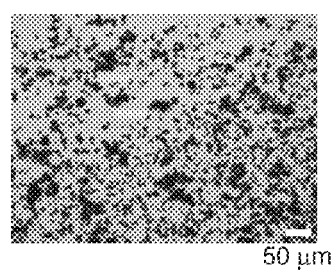
FIG. 4 shows an image obtained by microscopy of particles of the powder of FIG. 3.

An image obtained by microscopy is shown in FIG. 4.

Example 3—Stability Studies 3.1. Experiment 1

A study of stability of the product obtained in example 1 is carried out by storing the dry product under an inert atmosphere and in the dark, at a temperature of 5° C., for a period of 3 months.

At times T=0, T=1 month and T=3 months, a sample of product is taken and subjected to all the tests described in example 2.

By way of comparative example, the same experiment is carried out on a product obtained by means of the preparation process of the prior art described in document WO 2011/039432, providing in particular a molar deficiency in DL-lysine (more specifically, with an acetylsalicylic acid/DL lysine molar ratio equal to 1/0.89).

The results obtained are shown in table 2 hereinafter.

TABLE 2 results of stability tests for a product obtained by means of a
method in accordance with the invention and by means
of the process described in document WO 2011/039432

| Test | Specifications | Method in accordance with the invention | | | Process of WO 2011/039432 | | |
|---|---|---|---|---|---|---|---|
| | | Time (months) | | | | | |
| | | 0 | 1 | 3 | 0 | 1 | 3 |
| pH of the reconstituted solution | 4.5 to 6.5 | 5.9 | 5.6 | 5.5 | 5.2 | 5.2 | 5.1 |
| Water content (%) | ≤0.5 | 0.4 | 0.5 | 0.3 | — | — | — |
| Residual moisture content (%) | ≤1.0 | 0.4 | 0.6 | 0.6 | 0.72 | 0.61 | 0.61 |
| HPLC content of acetylsalicylic acid (%) | 97.0 to 101.0 | 98.3 | 98.5 | 98.8 | 93.6 | 90.0 | 91.6 |
| Impurities (%) | | | | | | | |
| Salicylic acid | ≤0.3 | 0.13 | 0.17 | 0.21 | 1.9 | 1.9 | 2.0 |
| Other unknown impurity | ≤0.1 | 0.02 | 0.02 | 0.02 | — | 0.026 | 0.027 |
| Sum of the impurities | — | 0.15 | 0.22 | 0.25 | — | 0.09 | 0.07 |

For all the conditions tested, the powder has an appearance which complies (fine, white, crystalline powder), as does the reconstituted solution (transparent solution).

As can be noted, the product obtained by means of the method in accordance with the invention of example 1 remains stable over time, throughout the experiment, and complies with the pharmacopeia specifications, in particular in terms of contents of acetylsalicylic acid and of salicylic acid, which is the main degradation product thereof.

In comparison, the product obtained by means of a process of the prior art exhibits much less stability over time. The initial degree of purity of the product is also not satisfactory.

3.2. Experiment 2

A study of stability of the product obtained in example 1 (new synthesis batch) is carried out by storing the dry product under an inert atmosphere and in the dark, at a temperature of 5° C., for a period of 6 months.

At times T=0, T=1 month, T=3 months and T=6 months, a sample of product is taken and subjected to all the tests described in example 2.

The results obtained are indicated in table 3 hereinafter.

TABLE 3 results of stability tests for a product obtained by
means of a method in accordance with the invention

| Time (months) | Specifications | 0 | 1 | 3 | 6 |
|---|---|---|---|---|---|
| Appearance of the powder | Crystalline white/fine | C | C | C | C |
| Appearance of the reconstituted solution | Transparent | C | C | C | C |
| pH of the reconstituted solution | 4.5 to 6.5 | 5.7 | 5.8 | 5.4 | 6.3 |
| Water content (%) | ≤0.5 | 0.4 | 0.3 | 0.3 | 0.3 |
| Residual moisture content (%) | ≤1.0 | 0.7 | 0.5 | 0.6 | 0.6 |
| HPLC content of acetylsalicylic acid (%) | 97.0 to 101.0 | 97.5 | 97.5 | 98.1 | 97.5 |

TABLE 3-continued results of stability tests for a product obtained by
means of a method in accordance with the invention

| Time (months) | Specifications | 0 | 1 | 3 | 6 |
|---|---|---|---|---|---|
| Impurities (%) | | | | | |
| Salicylic acid | ≤0.3 | 0.28 | 0.28 | 0.29 | 0.30 |
| Other unknown impurity | ≤0.1 | 0.03 | 0.03 | 0.03 | 0.03 |
| Sum of the impurities | | 0.32 | 0.33 | 0.33 | 0.34 |

C = complies

As can be noted, the product obtained by means of the method in accordance with the invention of example 1 remains stable over time and complies with the pharmacopeia specifications, throughout the experiment, including after 6 months of storage.

The slight differences noted compared with experiment 1, for the same product, can be attributed to the uncertainties associated with the assay methods, and are not significant.

Example 4—Comparative Examples

The synthesis method described in example 1 is carried out, but in different initial acetylsalicylic acid/DL-lysine molar ratios, more specifically molar ratios respectively of 1/0.977 (comparative example C1) and 1/1.034 (comparative example C2), very close to those recommended by the prior art.

A method in accordance with the invention, with an acetylsalicylic acid/DL-lysine molar ratio of 1/1, is carried out in parallel (example Inv.).

The operating conditions implemented are strictly identical, with the exception of the flow rate of the pumps. For each of the examples, these flow rates of the pumps are indicated in table 4 hereinafter.

TABLE 4 operating conditions for synthesis of the comparative products
C1 and C2, and of the product according to the invention Inv.

| Example | Pump flow rate solution A (l/h) | Pump flow rate solution B (l/h) | Acetylsalicylic acid/lysine molar ratio |
|---|---|---|---|
| Inv. | 13.07 | 4.47 | 1/1 |
| C1 | 13.07 | 4.37 | 1/0.977 |
| C2 | 13.07 | 4.62 | 1/1.034 |

After drying, the amounts of dry product indicated in table 5 hereinafter are obtained for each example.

A sample of each of these products is subjected to HPLC analysis, as described in example 2 above, in order to determine its acetylsalicylic acid content. The results obtained are indicated in table 5 hereinafter.

TABLE 5 results of analysis of the products obtained, for a product in accordance
with the invention Inv. and comparative products C1 and C2

| Example | Amount of dry product obtained (g) | HPLC content of acetylsalicylic acid (%) | HPLC content of salicylic acid (%) |
|---|---|---|---|
| Inv. | 427.88 | 98.3 | 0.13 |
| C1 | 351.86 | 92.2 | 1.4 |
| C2 | 437.41 | 90 | 1.7 |

As can be noted, the HPLC data clearly demonstrate that the comparative products C1 and C2, obtained using molar ratios different than the 1/1 molar ratio recommended by the present invention, although very close, have an acetylsalicylic acid content that is much lower than that of the product obtained in accordance with the present invention, and a much higher content of the major impurity, salicylic acid. These comparative products do not comply, in terms of purity, with the pharmacopeia specifications.

Example 5—Synthesis of DL-lysine Acetylsalicylate with a Recrystallization Step 5.1. Synthesis Method DL-lysine acetylsalicylate (III) is prepared from acetylsalicylic acid (I) and DL-lysine (II), as described in example 1 above, the only difference being that, after the first filtration step, 220 g of the product obtained are subjected to a recrystallization step.

This step is carried out according to the following operating protocol:
  the 220 g of product are suspended in 440 ml of 2-propanol;
  440 ml of water are added to the mixture, so as to dissolve the product,
  880 ml of 2-propanol are added to the medium,
  the temperature of the medium is decreased to approximately 25° C., and the recrystallization is initiated by additions of lysine acetylsalicylate crystals,
  the temperature of the medium is decreased to approximately 5° C., over the course of approximately 5 minutes.

At the end of these operations, crystals have formed in the medium.

The medium is subjected to a step of filtration under reduced pressure of 270 mbar, then to a drying step, in three distinct phases, according to the protocol described in example 1 above.

In the end, 176.56 g (recrystallization step yield: 80.3%) of a dry product which is in the form of a fine white crystalline powder are obtained. A sample of this dry product is taken from the filter, under an inert atmosphere, and subjected to the following various analyses.

5.2. Analyses

The analysis protocols are identical to those described in example 2 above.

Figure 5:
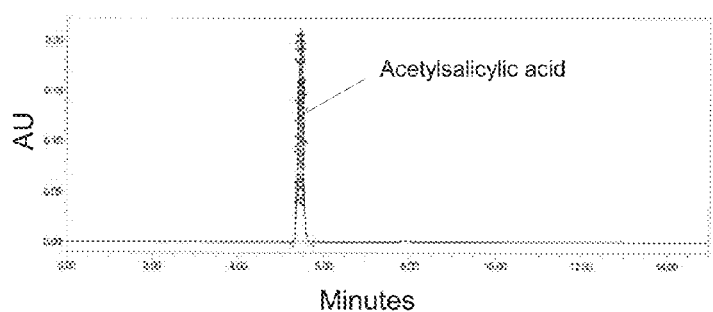
FIG. 5 shows an HPLC chromatogram obtained for a solution of DL-lysine acetylsalicylate obtained by means of a method in accordance with the invention, comprising a recrystallization step.

The acetylsalicylic acid content of the solid product obtained is determined by HPLC. The chromatogram obtained is shown in FIG. 5 (peak at 5.431 minutes). An acetylsalicylic acid titer of 98.5% is deduced therefrom.

The results obtained for the other parameters analyzed are indicated in table 6 hereinafter.

TABLE 6 result of analyses of the DL-lysine acetylsalicylate obtained
by means of a method according to one particular embodiment
of the invention comprising a recrystallization step

| Test | Recrystallized ASL |
|---|---|
| Appearance of the powder | White fine crystalline |
| Appearance of the reconstituted solution | Transparent clear |
| Water content | 0.11% |
| Salicylic acid content | 0.24% |
| Content of other impurities | 0.05% |

It emerges from these results, combined with that obtained for the HPLC assay of the acetylsalicylic acid content indicated above, that the method carried out makes it possible to obtain a salt of acetylsalicylic acid and DL-lysine with a high degree of purity, and which complies with the European Pharmacopeia specifications.

Figure 6:
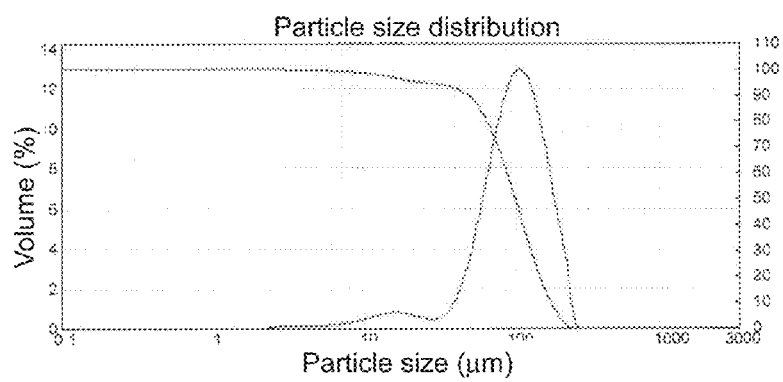
FIG. 6 is a graph indicating the size and the size distribution of the particles of a recrystallized DL-lysine acetylsalicylate powder obtained by means of a method in accordance with the invention, after drying.

The particle size was also analyzed by means of a Scirocco 2000 instrument (Malvern), according to a protocol conventional in itself. The results obtained, in terms of particle size, are shown in FIG. 6. The average particle size is 104.219 μm.

Figure 7:
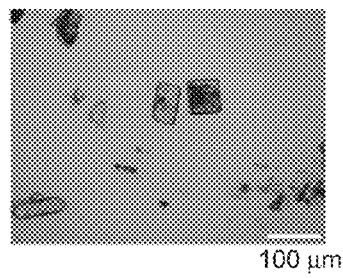
FIG. 7 shows an image obtained by microscopy of particles of the powder of FIG. 6.

An image of the recrystallized ASL powder, obtained by microscopy, is shown in FIG. 7.

These results show that the recrystallized lysine acetylsalicylate powder obtained has a narrow size distribution, with an average particle diameter of 104.219 μm.

The invention claimed is:

1. A method for preparing a salt of acetylsalicylic acid and a basic amino acid, which comprises mixing a solution of acetylsalicylic acid and a solution of said basic amino acid in a reactor, at a temperature of less than or equal to 30° C. at atmospheric pressure, wherein said mixing is carried out by gradual introduction simultaneously of said solution of acetylsalicylic acid and of said solution of said basic amino acid into the reactor, under conditions such that, throughout said introduction, at each instant amounts of acetylsalicylic acid and of said basic amino acid introduced into the reactor are equimolar.

2. The method as claimed in claim 1, comprising a crystal maturation phase, wherein a reaction medium, formed at the end of the introduction of the solution of acetylsalicylic acid and of the solution of said basic amino acid into the reactor, is kept with stirring at a temperature of between −15° C. and 20° C. for a period of between 30 and 90 minutes.

3. The method as claimed in claim 2, wherein, at the end of the crystal maturation phase, a solid contained in the reaction medium is isolated, then washed with an organic solvent.

4. The method as claimed in claim 2, wherein, at the end of the crystal maturation phase, a solid contained in the reaction medium is subjected to a step of recrystallization of the salt of acetylsalicylic acid and said basic amino acid, after having been isolated from the reaction medium.

5. The method as claimed in claim 4, wherein said recrystallization step is carried out in a mixture of solvents comprising at least one alcohol and water.

6. The method as claimed in claim 1, comprising a final step of drying the salt of acetylsalicylic acid and said basic amino acid obtained, said drying being carried out in at least two successive steps, comprising:
   a first step of drying with stirring, at a first pressure of between 200 and 300 mbar and at a first temperature of between 20 and 25° C., for a period of between 90 and 250 minutes; and
   a second step of drying with stirring, at a second pressure of between 10 and 30 mbar and at a second temperature of between 40 and 50° C., for a period of between 90 and 250 minutes.

7. The method as claimed in claim 6, wherein an intermediate drying step is carried out between the first drying step and the second drying step, said intermediate drying step being carried out with stirring, at a temperature between the first temperature and the second temperature, and at a pressure of between 200 and 300 mbar for a period of between 60 and 100 minutes, then at a pressure of between 10 and 30 mbar for a period of between 60 and 100 minutes.

8. The method as claimed in claim 1, wherein the acetylsalicylic acid solution comprises from 0.8 to 0.9 mol/l of acetylsalicylic acid, in a water-miscible organic solvent.

9. The method as claimed in claim 1, wherein the solution of said basic amino acid is an aqueous solution comprising from 4.5 to 5.5 mol/l of said basic amino acid.

10. The method as claimed in claim 1, wherein the gradual introduction of the solution of acetylsalicylic acid and of the solution of said basic amino acid into the reactor is carried out with a flow rate of introduction of the acetylsalicylic acid solution into the reactor of between 10 and 50 l/h, and a flow rate of introduction of the acetylsalicylic basic amino acid solution into the reactor of between 2 and 15 l/h.

11. The method as claimed in claim 1, wherein the basic amino acid is chosen from the group consisting of lysine, arginine, histidine and ornithine.

12. The method as claimed in claim 1, wherein all of the steps are carried out under an inert atmosphere.

13. A salt of acetylsalicylic acid and of a basic amino acid produced according to the method as claimed in claim 1, which is in granular form, having an average grain diameter of between 100, wherein the basic amino acid is lysine and 110 μm.

14. A method as claimed in claim 2, wherein during the crystal maturation phase the reaction medium is kept with stirring at 10° C. for a period of between 30 and 90 minutes.

15. A method as claimed in claim 2, wherein during the crystal maturation phase the reaction medium is kept with stirring at a temperature of between −15° C. and 20° C. for a period of 1 hour.

16. A method as claimed in claim 2, wherein at the end of the crystal maturation phase, a solid contained in the reaction medium is subjected to a step of recrystallization of the salt of acetylsalicylic acid and said basic amino acid, after having been isolated from the reaction medium, then washed with an organic solvent.

17. The method as claimed in claim 8, wherein the water-miscible organic solvent comprises acetone.

* * * * *